US00PP08027P

United States Patent [19]

Wilhelm

[11] Patent Number: Plant 8,027

[45] Date of Patent: Nov. 10, 1992

[54] HYBRID RASPBERRY CV. "HOLLINS"

[75] Inventor: Stephen Wilhelm, Oakland, Calif.

[73] Assignee: Sweetbriar Development Inc., Watsonville, Calif.

[21] Appl. No.: 713,704

[22] Filed: Jun. 11, 1991

[51] Int. Cl.[5] ..... A01H 5/00

[52] U.S. Cl. ..... Plt./46.2

[58] Field of Search ..... Plt./46.2

*Primary Examiner*—James R. Feyrer

*Attorney, Agent, or Firm*—Synnestvedt & Lechner

[57] ABSTRACT

The invention concerns a new and distinct variety of hybrid raspberry, the variety being particularly characterized and distinguished by the early fruiting of both the primocane and floricane crops; the primocanes bearing approximately one half of the total of the combined primocane and floricane crops; the fruit has a bright red color with only a slight tendency to darken or develop a waxy bloom; the drupelets are of substantially uniform size and have only a slight median drupelet groove; the fruit is firm and compact with a ring of tight fitting drupelets at its collar; and even after relatively warm central California coastal winters the floricane budbreak is good. The new variety holds its distinguishing characteristics through succeeding propagations by planting dormant root cuttings, dormant canes and non-dormant root shoot cuttings.

6 Drawing Sheets

This invention relates to a new variety of hybrid raspberry cv. "Hollins" that was discovered and asexually reproduced by Stephen Wilhelm. It has as its seed parent "Sweetbriar" (U.S. Plant Pat. No. 4,486) and as its pollen parent Reiter E4720 (unpatented).

The new raspberry cv. "Hollins" is particularly distinguishable from other commercialized raspberry cultivars by the following combination of characteristics: the early fruiting of both the primocane and floricane crops, the primocanes bearing approximately one half of the total of the combined primocane and floricane crops; the fruit has a bright red color with only a slight tendency to darken or develop a waxy bloom; the drupelets are of substantially uniform size and have only a slight median drupelet groove; the fruit is firm and compact with a ring of tight fitting drupelets at its collar; and even after relatively warm central California coastal winters the floricane budbreak is good. The new variety holds its distinguishing characteristics through succeeding propagations by planting dormant root cuttings, dormant canes and non-dormant root shoot cuttings.

The new raspberry cultivar "Hollins" may be distinguished from its pollen parent Reiter E4720 by the following combination of characteristics: the "Hollins" cultivar normally begins growth later in the spring than Reiter E4720, yields more attractive fruit and has a longer primocane fruiting cycle.

The new raspberry cultivar "Hollins" may be distinguished from its seed parent cv. "Sweetbriar" (U.S. Plant Pat. No. 4,486) by the following combination of characteristics: "Hollins" is more resistant to powdery mildew and late leaf rust; is earlier fruiting by 10–14 days in both the primocane and floricane crops; it is of a more compact growth habit; its berries are more uniform in shape and in drupelet size. The berries are brighter in appearance and Hollins has a less pronounced median drupelet groove.

The accompanying drawing illustrates the new raspberry variety cv. "Hollins" in color as grown in Watsonville, Calif. and shows the flowering and fruiting thereof from bud to full flower and fruit.

Figure 1:
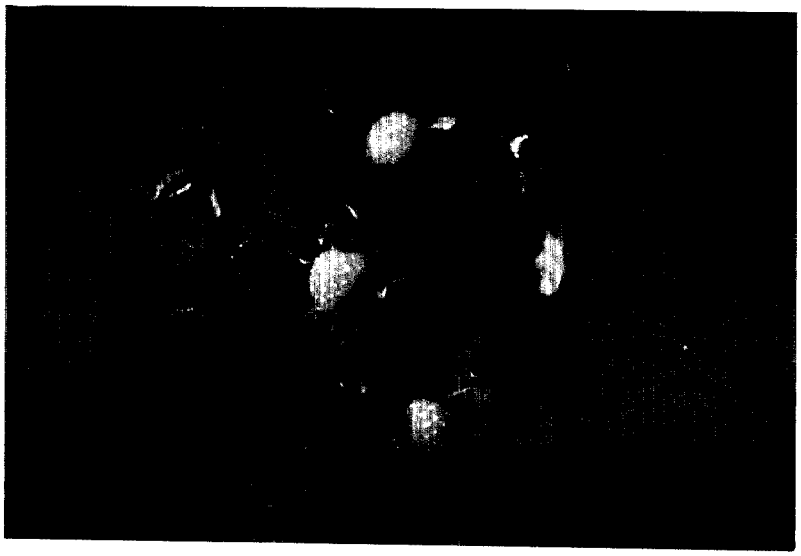
FIG. 1 is a photograph of a fruiting primocane showing fruit in various stages of development.
Figure 2:
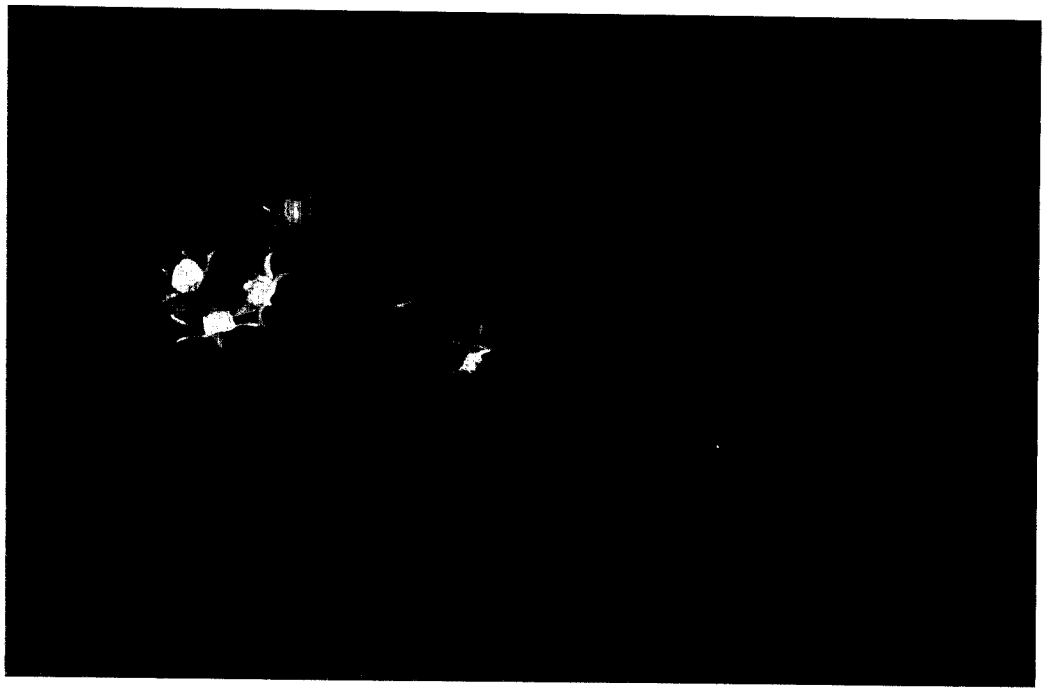
FIG. 2 is a photograph of a fully expanded leaf (at the right) and younger leaves with flowers and developing fruit (at the left).
Figure 3:
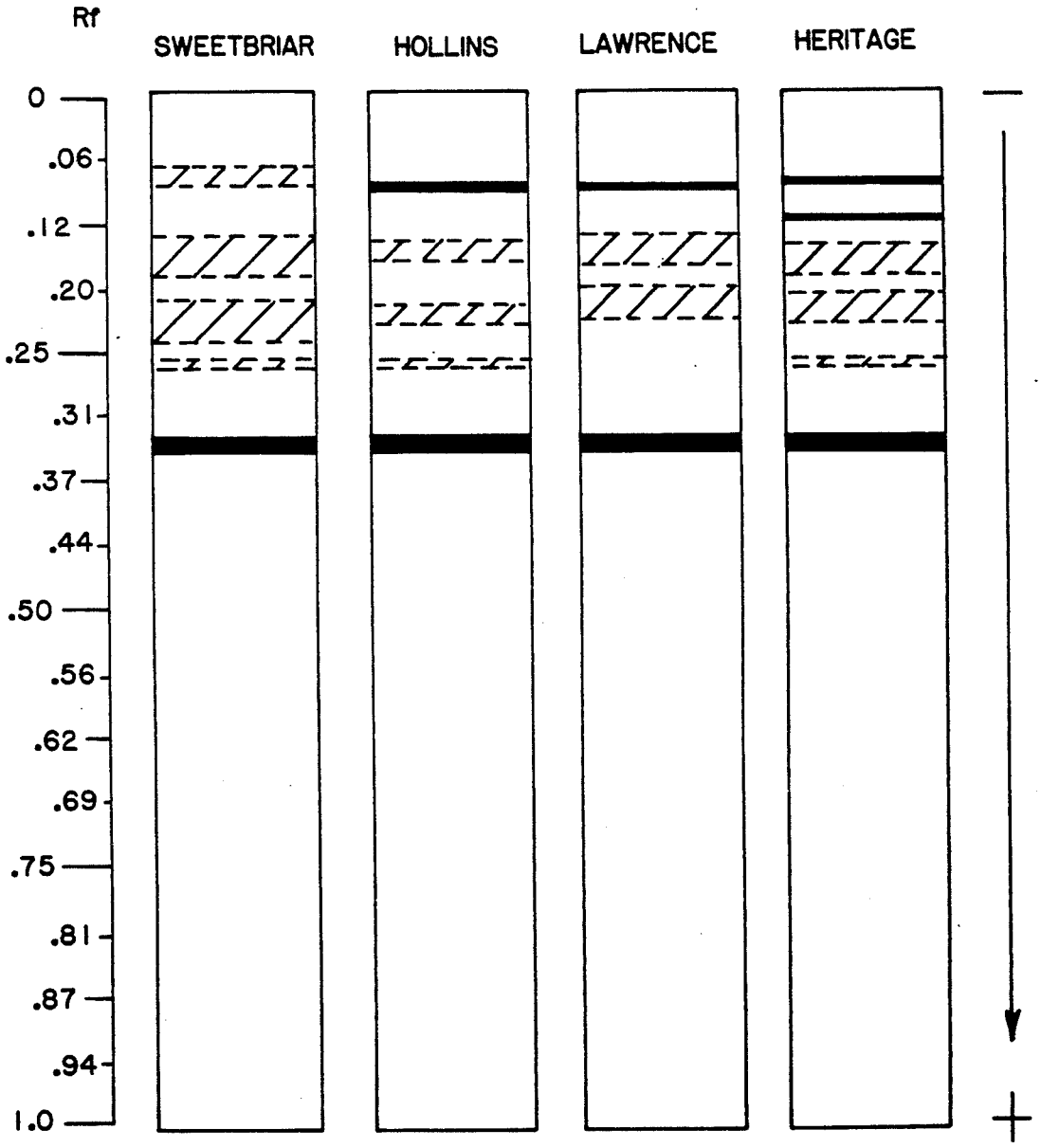
FIGS. 3, 4, 5 and 6 illustrate the isoenzyme separation and banding patterns of Sweetbriar, Heritage, Lawrence and Hollins raspberry varieties after polyacrylamide gel electrophoresis.
Figure 4:
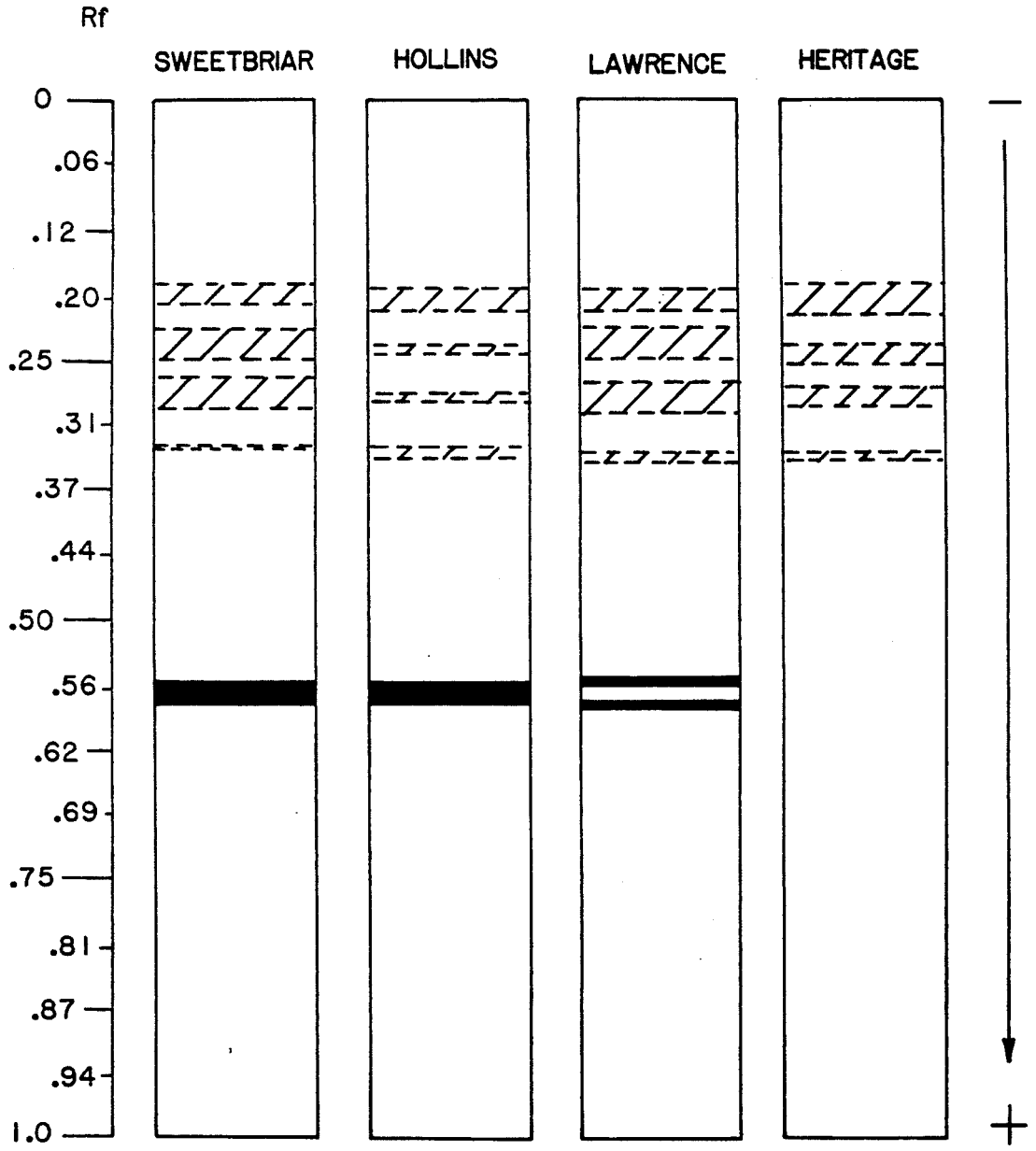
Figure 5:
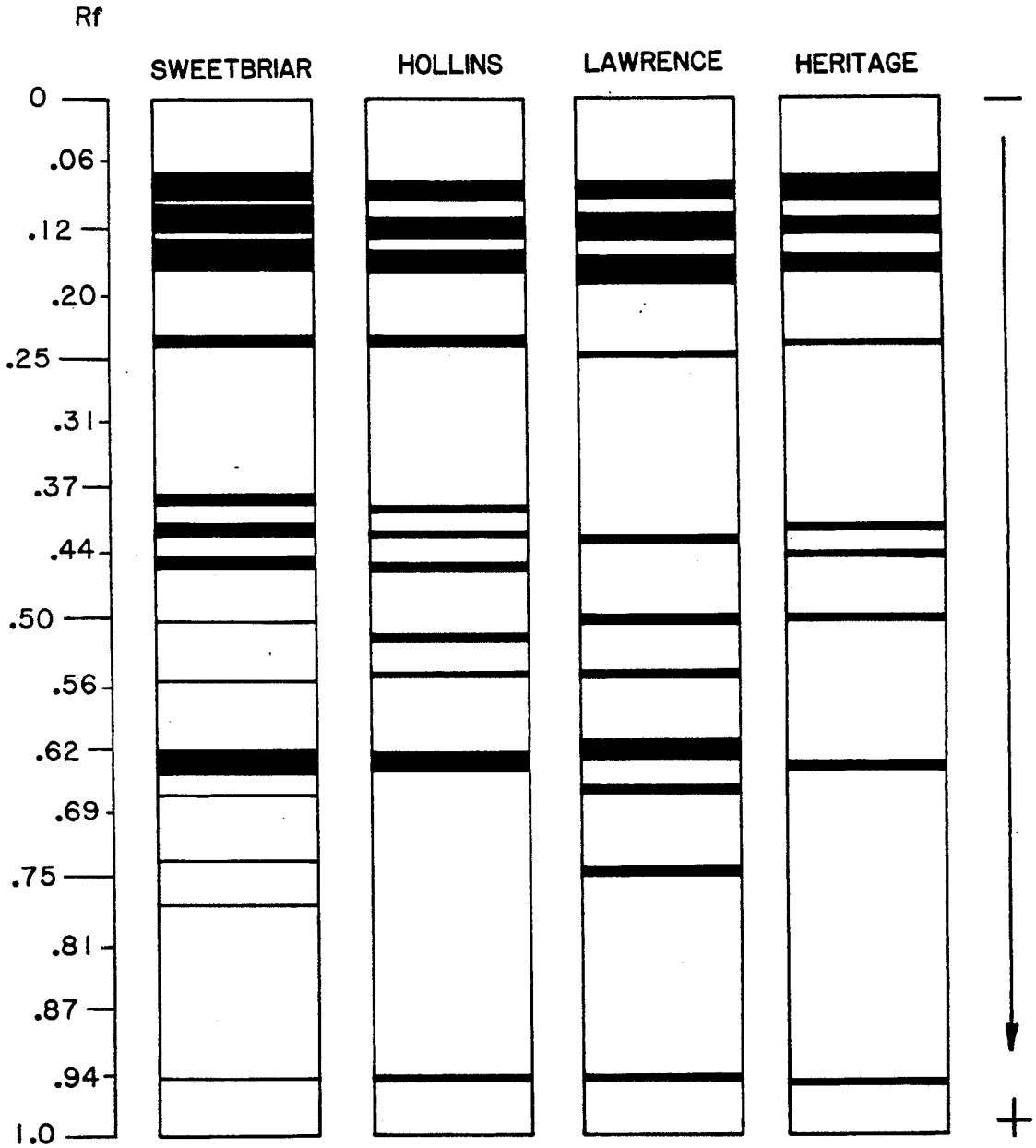
Figure 6:
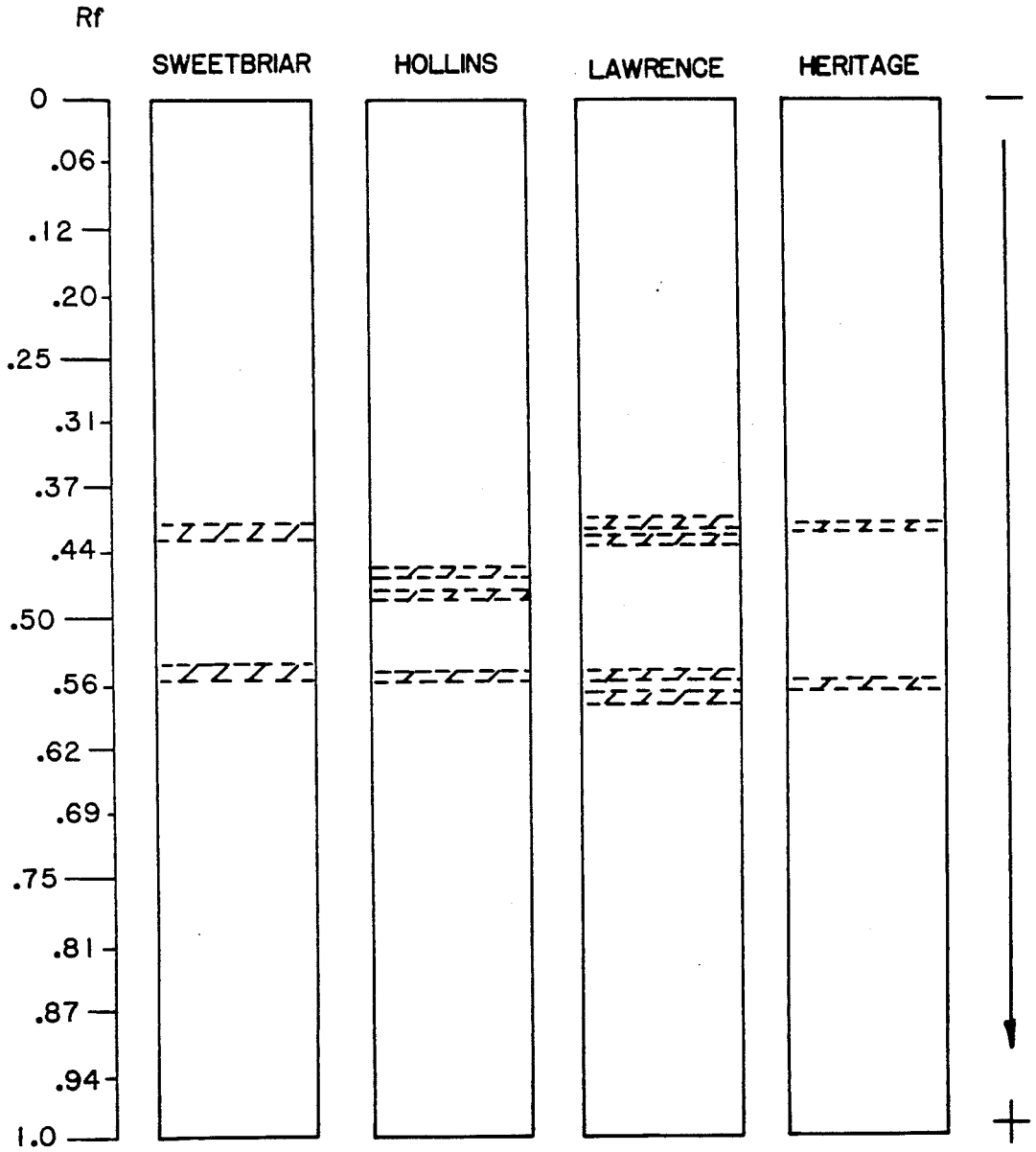
Figure 7:
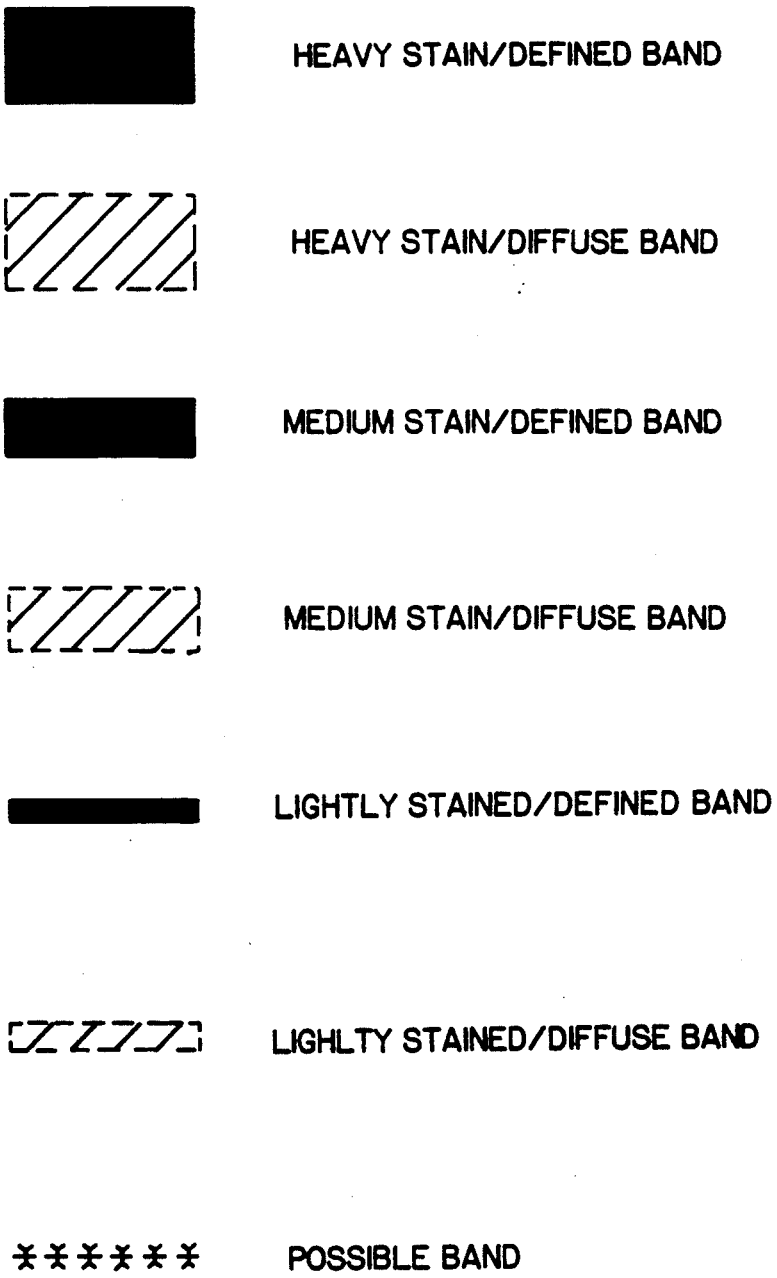
FIG. 7 is the legend for the banding patterns shown in FIGS. 3–6, inclusive.

Throughout this specification, color names beginning with a small letter signify that the name of that color as used in common speech is aptly descriptive. Color names beginning with a capital letter designate color values based on The R.H.S. Colour Chart published by The Royal Horticultural Society of London, England.

The descriptive matter which follows pertains to raspberries grown in Watsonville, Calif., in 1989 and 1990 and is believed to apply to similar conditions of soil and climate elsewhere.

PLANT

The plant is a deciduous medium sized bush of erect habit. It has medium dense foliage and exhibits good berry productivity with early fruiting on both primocanes and floricanes. From 50 to 60% of the cane length of the primocanes flower the year of planting. Flowering of primocanes begins about six months after the usual date of planting dormant propagating material (usually December in the Watsonville area). Floricanes begin producing berries in May of the year following the primocane crop. The primocanes bear about one half of the total primocane/floricane berry crops. The plants can withstand temperatures at least as low a 26° F. in mid-winter without freeze damage. They have an average or medium suckering tendency.

CANES

A medium number (i.e., from 3 to 7) of young shoots or primocanes are produced on the crown per growing season. There is a strong bright red anthocyanin coloration in leaves of very young shoots. Prior to dormancy the primocanes reach maximum size and are of medium (about 54" to 66") length. Dormant primocanes have a diameter of about 0.27" to 0.33" in the central third of the cane. In cross-section the canes have weak depressions — a somewhat pentagonal shape. A few rigid small (1 mm to 1.5 mm in length) pigmented spines are present on the young shoots and mature primocanes and they are positioned in a horizontal attitude relative to the cane axis. Spines are also irregularly distributed on the petioles. The internodes are short, averaging about 1" to 2½" between nodes. Lenticels are not visually detectable.

On the floricanes the lateral shoots are about 18" to 24" in length, self-supporting and Yellow-Green 154B in Color. There are a medium number of lateral shoots per cane (between about 14 to 23). In the mid-cane area, the lateral shoots have an average of about 10 nodes each. The average number of flowers in the midcane area (e.g. 4th node from apex) is between about 2 and 3 per node.

LEAVES

The leaves are compound and trifoliate and the lateral leaflets overlap the terminal leaflet. Basal leaflets are opposite. The rachis between the lateral leaflets and the terminal leaflet usually has a length of about 1¼" to 2".

The average mature terminal leaflet is between about 4" to 6" in length and about 3" to 4¾" in width.

The average mature lateral leaflet is between about 3½ to 4" in length and 2½" to 3" in width.

Mature leaves are Yellow Green 147A on the face and Greyed Green 191 A on the underside. The veins on the underside are Yellow Green 148C. The faces and undersides of the leaves are weakly glossy. In shape the basal leaflets are ovate acuminate and the terminal leaflets are ovate acuminate to cordate. Leaf margins are serrate. The terminal leaflet shows only a slight tendency to cup downward and less than the parent "Sweetbriar". The terminal leaflets are prominently rugose with distinct ridges and alternate valleys traversing the leaf from mid region to blade edge.

FLOWERS

In Watsonville, Calif., primocanes have a blossom period from about June 15 until the first fall frost. Floricanes blossom from about March 15 until June 1. The primary color of the flower is White 155D. The flowers have five petals in free arrangement and the petals average about 3.5 mm to 5.0 mm in width. Pubescence is absent on the petals. The pedicels show a weak anthocyanin coloration. The flowers are self-fertile and will develop fruit after self-pollination.

FRUIT

The primocane fruit crop is early ripening beginning to ripen about July 20 and has an average length harvest period. The fruit is glossy and has a coloration of about Red 45B when mature. From July to September the average berry weighs about 4.0 grams.

The floricane fruit crop is also early ripening; beginning to ripen about May 1 and ripens uniformly throughout a long harvest period (about 60 to 75 days).

When immature, the floricane fruit is neither glossy nor dull (i.e., neutral) and is about Red 40D in color; the maturing fruit darkens to about Red 42D in color and is neither glossy nor dull. When mature and fully ripe the fruit darkens to between about Red 45A and 46A and becomes glossy with only a slight tendency to develop a waxy bloom.

Berries harvested from floricanes during May and June have an average weight of from about 2.5 to 3.0 grams. The berries have, in longitudinal section, a circular to ovate shape; the axial length is from about 0.45" (1.2 cm) to 0.79" (2.0 cm.) and the axial diameter ranges from 0.71" (1.8 cm) to 0.79" (2.0 cm).

The fruit has from about 76 to 90 small smooth and substantially uniformed size drupelets per berry. The drupelets at the open end that forms the berry collar are tight fitting and forming a uniformly structured ring or circlet of drupelets. The seeds are of medium hardness and of a small size —0 weighing on the average from 1.45 mg. to 1.56 mg. after drying at room temperature for six days.

The mature fruit is sub-acid in flavor and has a slight aroma and mild acidity. After ripening, the unpicked fruit will remain firm for about 2 days (or more if the ambient temperature is cool) and is weakly attached to the receptacle. The fruit cavity is of medium size and the receptacle is generally conical in shape. The fruit shows average resistance to bruising when hand picked. The picked fruit has good shipping qualities.

Both foliage and fruit show high resistance to strains prevalent in the Watsonville area of powdery mildew and late leaf rust.

In addition to the foregoing biological or morphological description and to provide further means for identifying the new variety and distinguishing it from some other somewhat similar and/or related raspberry varieites, the variety has been analyzed to obtain an indication of its genetic makeup. Specifically, fruit of the Lawrence (U.S. Plant patent application Ser. No. 713,952, filed Jun. 11, 1991), Hollins (the variety of this application), Heritage (a well-known raspberry cultivar) and Sweetbriar (the seed parent of both Hollins and Lawrence) raspberry varieties was electrophoretically analyzed on polyacrylamide gel slabs to determine the characteristic isoenzyme separation and banding patterns of each variety with respect to Acid Phosphatase, Peroxidase, Esterase and Leucine Aminopeptidase.

The enzyme stains selected for the gel electrophoresis analysis were suggested by data presented in S. Arulsekar and D. E. Parfitt, *Isozyme Analysis Procedures for Stone Fruits, Almond, Grape, Walnut, Pistachio and Fig, Hortscience* 21(4):928–33 (1986), and J. C. Cousineau and D. S. Donnelly, *Identification of Raspberry Cultivars by Starch Gel Electrophoresis and Isoenzyme Staining,* Acta Horticulture, 262:259–67 (1989). The results of the electrophoresis analysis are set forth below.

TABLE 1

| | ACID PHOSPHATASE | | | |
|---|---|---|---|---|
| Rf | SWEET-BRIAR | HOLLINS | LAWRENCE | HERITAGE |
| .075–.100 | | 1 | 1 | 1 |
| .100–.125 | | | | 1 |
| .150–.175 | 1 | | 1 | 1 |
| .175–.200 | | 1 | | |
| .225–.250 | 1 | 1 | 1 | 1 |
| .300–.325 | 1 | 1 | 1 | 1 |

TABLE 2

| | PEROXIDASE | | | |
|---|---|---|---|---|
| Rf | SWEET-BRIAR | HOLLINS | LAWRENCE | HERITAGE |
| .200–.225 | 1 | 1 | 1 | 1 |

TABLE 2-continued

| | PEROXIDASE | | | |
|---|---|---|---|---|
| Rf | SWEET-BRIAR | HOLLINS | LAWRENCE | HERITAGE |
| .225-.250 | 1 | 1 | | 1 |
| .275-.300 | 1 | 1 | 1 | 1 |
| .575-.600 | | | 1 | |
| .625-.650 | 1 | 1 | 1 | |

TABLE 3

| | ESTERASE | | | |
|---|---|---|---|---|
| Rf | SWEET-BRIAR | HOLLINS | LAWRENCE | HERITAGE |
| .075-.100 | 1 | 1 | 1 | 1 |
| .100-.125 | 1 | 1 | 1 | 1 |
| .150-.175 | 1 | 1 | 1 | 1 |
| .200-.225 | | 1 | | |
| .225-.250 | 1 | | 1 | 1 |
| .375-.400 | 1 | 1 | | |
| .400-.425 | 1 | 1 | 1 | 1 |
| .425-.450 | 1 | | | 1 |
| .450-.475 | | 1 | | |
| .475-.500 | 1 | | 1 | 1 |
| .500-.525 | | 1 | | |
| .525-.550 | | | 1 | |
| .550-.575 | 1 | 1 | | |
| .625-.650 | 1 | | 1 | |
| .650-.675 | 1 | 1 | | 1 |
| .675-.700 | | | 1 | |

TABLE 3-continued

| | ESTERASE | | | |
|---|---|---|---|---|
| Rf | SWEET-BRIAR | HOLLINS | LAWRENCE | HERITAGE |
| .725-.750 | 1 | | | |
| .750-.775 | | | 1 | |
| .775-.800 | 1 | | | |
| .925-.950 | 1 | 1 | 1 | 1 |

TABLE 4

| | LEUCINE AMINOPEPTIDASE | | | |
|---|---|---|---|---|
| Rf | SWEET-BRIAR | HOLLINS | LAWRENCE | HERITAGE |
| .400-.425 | 1 | | 1-2 | 1 |
| .475-.500 | | 2 | | |
| .525-.550 | 1 | 1 | 2 | 1 |

In the analysis of the enzymatic comparisons with Sweetbriar and Heritage, the Hollins variety displays a significant difference in the banding patterns of Peroxidase and Esterase. Bands appear in the electrophoretic analysis of the Hollins variety which do not appear in the electrophoretic analysis of Sweetbriar and Heritage. In addition, the Hollins variety display a significant difference in the banding patterns of Peroxidase, Esterase and Leucine Aminopeptidase from Lawrence, a related variety of raspberry.

I claim:

1. A new variety of raspberry cv. "Hollins" as herein illustrated and described.

* * * * *